(12) United States Patent
Alder et al.

(10) Patent No.: US 10,183,136 B2
(45) Date of Patent: *Jan. 22, 2019

(54) DETERMINATION OF APNEA/HYPOPNEA DURING CPAP TREATMENT

(71) Applicant: ResMed Limited, Bella Vista (AU)

(72) Inventors: Matthew Alder, Wollongong (AU); Steven Paul Farrugia, Sydney (AU); Chinmayee Somaiya, Sydney (AU)

(73) Assignee: ResMed Limited (AU)

( * ) Notice: Subject to any disclaimer, the term of this patent is extended or adjusted under 35 U.S.C. 154(b) by 183 days.

This patent is subject to a terminal disclaimer.

(21) Appl. No.: 14/558,835

(22) Filed: Dec. 3, 2014

(65) Prior Publication Data

US 2015/0165145 A1 Jun. 18, 2015

Related U.S. Application Data

(63) Continuation of application No. 12/278,372, filed as application No. PCT/AU2007/000273 on Mar. 6, 2007, now Pat. No. 8,931,483.

(Continued)

(51) Int. Cl.
*A61M 16/00* (2006.01)
*A61B 5/087* (2006.01)
(Continued)

(52) U.S. Cl.
CPC ......... *A61M 16/0069* (2014.02); *A61B 5/087* (2013.01); *A61B 5/4818* (2013.01);
(Continued)

(58) Field of Classification Search
CPC ..... A61B 5/087; A61B 5/4818; A61B 5/4836; A61B 5/725; A61M 2016/003;
(Continued)

(56) References Cited

U.S. PATENT DOCUMENTS 4,944,310 A 7/1990 Sullivan
5,245,995 A 9/1993 Sullivan et al.
(Continued)

FOREIGN PATENT DOCUMENTS

EP 0651971 A1 5/1995
JP 2004-509743 A 4/2004
(Continued)

OTHER PUBLICATIONS

Extended European Search Report for Application No. EP07718546 dated Jun. 5, 2013.
(Continued)

*Primary Examiner* — Peter S Vasat
(74) *Attorney, Agent, or Firm* — Botos Churchill IP Law LLP (57) ABSTRACT

CPAP treatment apparatus is disclosed having a controllable positive airway pressure device. A sensor generates a signal representative of patient respiratory flow that is provided to a controller. The controller is operable to determine the occurrence of an apnea from a reduction in respiratory airflow below a threshold determined from long term ventilation. When an apnea or hypopnea has occurred the calculation of the threshold is suspended until the end of that event.

32 Claims, 6 Drawing Sheets

Related U.S. Application Data (60) Provisional application No. 60/779,625, filed on Mar. 6, 2006.

(51) Int. Cl.
*A61B 5/00* (2006.01)
*A61M 16/06* (2006.01)
*A61M 16/08* (2006.01)

(52) U.S. Cl.
CPC ............ *A61B 5/4836* (2013.01); *A61B 5/725* (2013.01); *A61B 5/7278* (2013.01); *A61B 5/7282* (2013.01); *A61M 16/0003* (2014.02); *A61M 16/0051* (2013.01); *A61M 16/024* (2017.08); *A61M 16/06* (2013.01); *A61M 16/0875* (2013.01); *A61M 2016/003* (2013.01); *A61M 2016/0021* (2013.01); *A61M 2016/0027* (2013.01); *A61M 2016/0036* (2013.01); *A61M 2205/3303* (2013.01); *A61M 2205/3334* (2013.01); *A61M 2205/50* (2013.01); *A61M 2230/40* (2013.01)

(58) Field of Classification Search
CPC ...... A61M 2205/3334; A61M 2205/50; A61M 2230/40
See application file for complete search history.

(56) References Cited

U.S. PATENT DOCUMENTS

| | | | |
|---|---|---|---|
| 5,704,345 A | 1/1998 | Berthon-Jones | |
| 6,179,784 B1* | 1/2001 | Daniels | A61B 5/083 600/529 |
| 6,305,374 B1* | 10/2001 | Zdrojkowski | A61M 16/0051 128/204.21 |
| 6,360,741 B2 | 3/2002 | Truschel | |
| 6,363,933 B1* | 4/2002 | Berthon-Jones | A61B 5/087 128/200.24 |
| 6,502,572 B1 | 1/2003 | Berthon-Jones et al. | |
| 6,675,797 B1 | 1/2004 | Berthon-Jones | |
| 2002/0165462 A1 | 11/2002 | Westbrook et al. | |
| 2003/0018241 A1 | 1/2003 | Mannheimer | |
| 2003/0111079 A1 | 6/2003 | Matthews et al. | |
| 2003/0121519 A1 | 7/2003 | Estes et al. | |
| 2003/0154979 A1* | 8/2003 | Berthon-Jones | A61M 16/00 128/204.18 |
| 2004/0123866 A1* | 7/2004 | Berthon-Jones | A61B 5/087 128/204.23 |
| 2004/0187870 A1 | 9/2004 | Matthews et al. | |
| 2005/0020932 A1 | 1/2005 | Haberland et al. | |
| 2005/0241639 A1 | 11/2005 | Zilberg | |
| 2006/0027234 A1* | 2/2006 | Gradon | A61M 16/10 128/204.21 |
| 2008/0053440 A1* | 3/2008 | Farrugia | A61M 16/00 128/204.23 |
| 2009/0020121 A1* | 1/2009 | Bassin | A61M 16/00 128/204.23 |

FOREIGN PATENT DOCUMENTS

| | | |
|---|---|---|
| JP | 2004535248 A | 11/2004 |
| JP | 2005-537041 A | 12/2005 |
| JP | 2007521889 A | 8/2007 |
| JP | 2009528858 A | 8/2009 |
| WO | 2000/078379 A1 | 12/2000 |
| WO | 0226392 A1 | 4/2002 |
| WO | 03098385 A2 | 11/2003 |
| WO | 2005011469 A2 | 2/2005 |
| WO | 2005077447 A1 | 8/2005 |
| WO | 2006014114 A1 | 2/2006 |

OTHER PUBLICATIONS

Japanese Office Action for Application No. 2012-097037 dated May 13, 2013.
Office Action from corresponding Japanese Application No. 2008-557550, dated Jan. 24, 2012.
Office Action from corresponding Japanese Application No. 2008-557550, dated Jun. 6, 2012.

* cited by examiner

DETERMINATION OF APNEA/HYPOPNEA DURING CPAP TREATMENT

CROSS-REFERENCE TO RELATED APPLICATIONS

The present application is a continuation of U.S. patent application Ser. No. 12/278,372, filed on Aug. 5, 2008, which application is a national phase entry under 35 U.S.C. § 371 of International Application No. PCT/AU07/00273 filed Mar. 6, 2007, which claims priority from U.S. Provisional Patent Application No. 60/779,625 filed Mar. 6, 2006, all of which are hereby incorporated herein by reference.

FIELD OF THE INVENTION

This invention relates to the administration of continuous positive airway pressure (CPAP) treatment for partial or complete upper airway obstruction by auto-titrating devices that adjust treatment pressure to eliminate obstructive airway events. In particular it relates to the detection of apnea/hypopnea events.

BACKGROUND OF THE INVENTION

In the Sleep Apnea syndrome a person stops breathing during sleep. Cessation of airflow for more than 10 seconds is called an "apnea". Apneas lead to decreased blood oxygenation and thus to disruption of sleep. Apneas are traditionally categorized as either central, where there is no respiratory effort, or obstructive, where there is respiratory effort. With some central apneas, the airway is open, and the subject is merely not attempting to breathe. Conversely, with other central apneas and all obstructive apneas, the airway is closed. The occlusion is usually at the level of the tongue or soft palate. The airway may also be partially obstructed (i.e., narrowed or partially patent). This also leads to decreased ventilation (hypopnea), decreased blood oxygenation and disturbed sleep.

The common form of treatment of these syndromes is the administration of Continuous Positive Airway Pressure (CPAP). The procedure for administering CPAP treatment has been well documented in both the technical and patent literature. An early description can be found in U.S. Pat. No. 4,944,310 (Sullivan). Briefly stated, CPAP treatment acts as a pneumatic splint of the airway by the provision of a positive pressure, usually in the range 4-20 cm $H_2O$. The air is supplied to the airway by a motor driven blower whose outlet passes via an air delivery hose to a nose (or nose and/or mouth) mask sealingly engaged to a patient's face. An exhaust port is provided in the delivery tube proximate to the mask. The mask can take the form of a nose and/or face mask or nasal prongs, pillows or cannulae.

Various techniques are known for sensing and detecting abnormal breathing patterns indicative of obstructed breathing. U.S. Pat. No. 5,245,995 (Sullivan et al.), for example, generally describes how snoring and abnormal breathing patterns can be detected by inspiration and expiration pressure measurements made while a subject is sleeping, thereby leading to early indication of preobstructive episodes or other forms of breathing disorder. Particularly, patterns of respiratory parameters are monitored, and CPAP pressure is raised on the detection of pre-defined patterns to provide increased airway pressure to, ideally, subvert the occurrence of the obstructive episodes and the other forms of breathing disorder. U.S. Pat. No. 6,502,572 (Berthon-Jones et al.) generally describes a CPAP treatment apparatus having a controllable flow generator (which is used herein as an example of a positive airway pressure device) operable to produce breathable gas at a treatment pressure elevated above atmosphere to a patient by a delivery tube coupled to a mask having connection with a patient's airway. A sensor generates a signal representative of patient respiratory flow that is provided to a controller. The controller is operable to determine the occurrence of an apnea from a reduction in respiratory airflow below a threshold, and if an apnea has occurred, to determine the duration of the apnea and to cause the flow generator to increase the treatment pressure. The '572 patent contains explicit pseudo-code for various algorithms involved in the determination of the presence of apneas and hypopnoeas, which is included herein by reference.

BRIEF SUMMARY OF THE INVENTION

The present invention is directed to an improvement in the apnea/hypopnea detection algorithm of such devices as disclosed by the '572 patent to simplify it, thereby reducing its memory demands, decrease its sensitivity to noise and to remove a problem with the determination of long term ventilation when apneas/hypopnoeas are present.

The invention discloses a method for the administration of CPAP treatment pressure comprising the steps of:

supplying breathable gas to the patient's airway at a treatment pressure;

determining a measure of respiratory airflow; and determining the occurrence of an apnea/hypopnea from a comparison of a threshold based upon long term ventilation with short term ventilation, wherein the determination of long term ventilation is not updated while an apnea/hypopnea event is in progress and the apnea/hypopnea event is considered terminated when there is an excess of above threshold values of the short term ventilation;

increasing the treatment pressure during the presence of the apnea/hypopnea.

The invention further discloses a CPAP treatment apparatus for implementing the above method comprising:

a controllable flow generator operable to produce breathable gas at a pressure elevated above atmosphere;

a gas delivery tube coupled to the flow generator;

a patient mask coupled to the tube to receive said breathable gas from the flow generator and provide said gas, at a desired treatment pressure, to the patient's airway;

a controller operable to receive input signals and to control operation of said flow generator and hence the treatment pressure; and a sensor located to sense patient respiratory airflow and generate a signal input to the controller from which patient respiratory airflow is determined;

and wherein the controller is operable to determine the occurrence of an apnea from a comparison of a threshold based upon long term ventilation with short term ventilation, wherein the determination of long term ventilation is not updated while an apnea/hypopnea event is in progress and the apnea/hypopnea event is considered terminated when there is an excess of above threshold values of the short term ventilation.

The recognition of the occurrence of an apnea begins by calculating an average respiratory airflow over a short time interval, calculating the average respiratory airflow over a longer time interval, and determining whether the average respiratory airflow over the short time interval is less than a predetermined fraction of the average respiratory airflow over the longer time interval, provided that the calculation over the longer time interval ceases until the apnea is terminated. For simplicity the averages may be calculated by using an IIR filter. Occurrence and termination of an apnea or hypopnea event is determined from the number of above threshold values of the short term ventilation.

In a preferred embodiment, the sensor can comprise a flow sensor, and the controller derives respiratory airflow therefrom.

The method and apparatus can also advantageously be used in concert with the 'forced oscillation method' for measuring airway patency (referred to above as European Publication No. 0 651 971 A1, U.S. Pat. No. 5,704,345 whose disclosure is hereby incorporated by reference), in which the CPAP pressure is modulated with an amplitude of for example 1 cmH$_2$O at 4 Hz, the induced airflow at 4 Hz is measured, the conductance of the airway calculated by dividing the amplitude of the induced airflow by the pressure modulation amplitude, and the additional requirement imposed that the treatment pressure is only increased if the conductance is greater than a threshold.

The present invention can be combined with an independent pressure increase in response to indicators of partial upper airway obstruction such as snoring or changes in shape of the inspiratory flow-time curve. In this way it is possible in most subjects to achieve pre-emptive control of the upper airway, with pressure increases in response to partial upper airway obstruction preventing the occurrence of closed airway apneas. In the minority of subjects in whom pre-emptive control is not achieved, this combination will also correctly increase the CPAP pressure in response to those closed airway apneas that occur at low CPAP pressure without prior snoring or changes in the shape of the inspiratory flow-time curve. Furthermore, the combination will avoid falsely increasing the CPAP pressure in response to open airway apneas induced by high pressure.

BRIEF DESCRIPTION OF THE DRAWINGS

Embodiments of the invention will now be described with reference to the accompanying drawings, in which.

DETAILED DESCRIPTION

Figure 1:
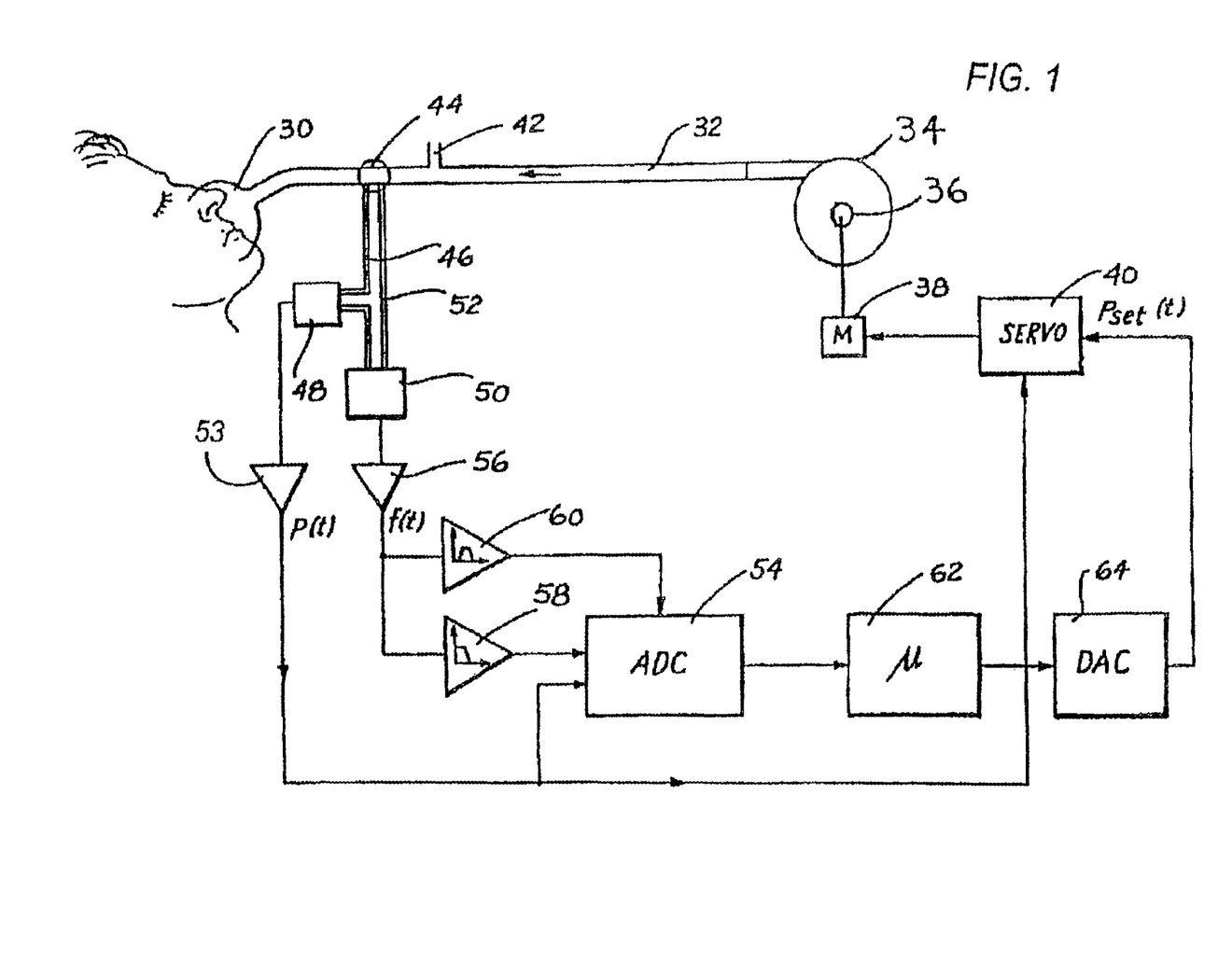
FIG. 1 shows, in diagrammatic form, apparatus embodying the invention.

FIG. 1 shows, in diagrammatic form, CPAP apparatus in accordance with one embodiment. A mask 30, whether either a nose mask and/or a face mask, is sealingly fitted to a patient's face. Breathable gas in the form of fresh air, or oxygen enriched air, enters the mask 30 by flexible tubing 32 which, in turn, is connected with a motor driven turbine or blower 34 to which there is provided an air inlet 36. The motor 38 for the turbine is controlled by a motor-servo unit 40 to commence, increase or decrease the pressure of air supplied to the mask 30 as CPAP treatment. The mask 30 also includes an exhaust port 42 that is close to the junction of the tubing 32 with the mask 30.

Interposed between the mask 30 and the exhaust 42 is a linear flow-resistive element 44. In practice, the distance between mask 30 and exhaust 42, including flow resistive element 44 is very short so as to minimize dead space volume. The mask side of the flow-resistive element 44 is connected by a first small bore tube 46 to a mask pressure transducer 48 and to an input of a differential pressure transducer 50. Pressure at the other side of the flow-resistive element 44 is conveyed to the other input of the differential pressure transducer 50 by a second small bore tube 52.

The mask pressure transducer 48 generates an electrical signal in proportion to the mask pressure, which is amplified by a first amplifier 53 and passed both to a multiplexer/ADC unit 54 and to the motor-servo unit 40. The function of the signal provided to the motor-servo unit 40 is as a form of feedback to ensure that the actual mask static pressure is controlled to be closely approximate to the set point pressure.

The differential pressure sensed across the linear flow-resistive element 44 is output as an electrical signal from the differential pressure transducer 50, and amplified by a second amplifier 56. The output signal from the second amplifier 56 therefore represents a measure of the mask airflow. The linear flow-resistive element 44 can be constructed using a flexible-vaned iris. Alternatively, a fixed orifice can be used, in which case a linearization circuit is included in the first amplifier 53, or a linearization step such as table lookup included in the operation of controller 62.

The output signal from the second amplifier 56 is low-pass filtered by the low-pass filter 58, typically with an upper limit of 10 Hz, in order to remove non-respiratory noise. The second amplifier 56 output signal is also bandpassed by the bandpass filter 60, and typically in a range of 30-100 Hz to yield a snoring signal. The outputs from both the low-pass filter 58 and the bandpass filter 60 are provided to the digitizer or ADC unit 54. The digitized respiratory airflow (FLOW), snore, and mask pressure ($P_{mask}$) signals from ADC unit 54 are passed to a controller 62, typically constituted by a micro-processor based device also provided with program memory 5 and data processing storage memory.

The controller 62 outputs a pressure request signal which is converted to a voltage by a DAC unit 64, and passed to the motor-servo unit 40. This signal therefore represents the set point pressure $P_{set}(t)$ to be supplied by the turbine or blower 34 to the mask 30 in the administration of CPAP treatment. The controller 62 is programmed to perform a number of processing functions.

As an alternative to the mask pressure transducer 48, a direct pressure/electrical solid state transducer (not shown) can be mounted from the mask with access to the space therewithin, or to the air delivery tubing 32 proximate the point of entry to the mask 30.

Figure 2:
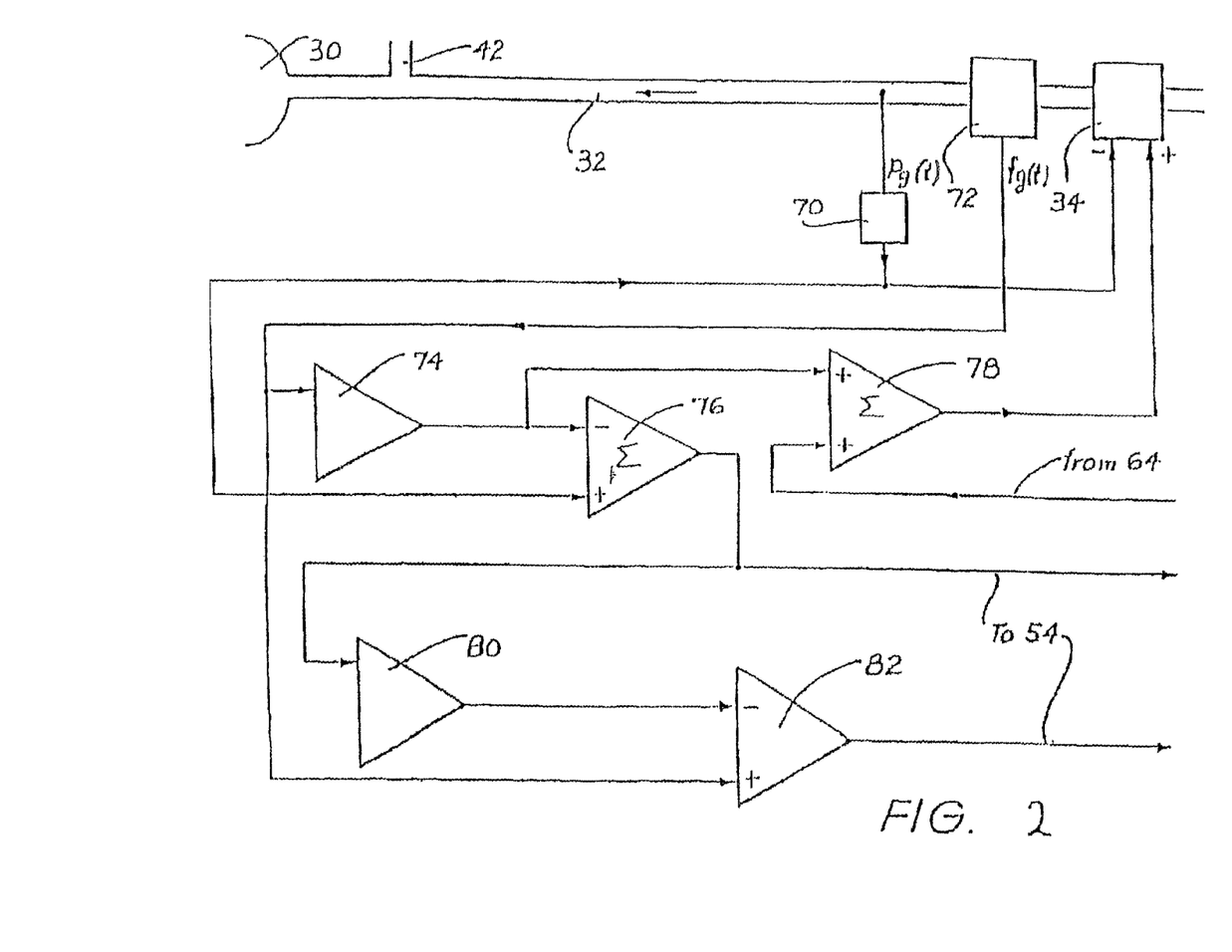
FIG. 2 shows an alternative arrangement of the apparatus of FIG. 1.

Further, it may not be convenient to mount the flow transducer or linear flow resistive element 44 at or near the mask 30, nor to measure the mask pressure at or near the mask. An alternative arrangement, where the flow and pressure transducers are mounted at or near the air pressure generator (in the embodiment being the turbine or blower 34) is shown in FIG. 2.

The pressure $p_g(t)$ occurring at the pressure generator or blower 34 outlet is measured by a pressure transducer 70. The flow $f_g(t)$ through tubing 32 is measured with flow sensor 72 provided at the output of the turbine or blower 34. The pressure loss along tubing 32 is calculated in pressure loss calculation element 74 from the flow through the tube $f_g(t)$, and a knowledge of the pressure-flow characteristic of the tubing, for example by table lookup. The pressure at the mask $p_m$ is then calculated in first subtraction element 76 by subtracting the tube pressure loss from $f_g(t)$.

The pressure loss along tube 32 is then added to the desired set pressure at the mask $P_{set}(t)$ in summation element 78 to yield the desired instantaneous pressure at the pressure generator. Preferably, the controller of the pressure generator has a negative feedback input from the pressure transducer 70, so that the desired pressure from summation element 78 is achieved more accurately. The flow through the exhaust 42 is calculated from the pressure at the mask (calculated in first subtraction element 76) from the pressure-flow characteristic of the exhaust in exhaust flow calculation element 80, for example by table lookup. Finally, the mask flow is calculated by subtracting the flow through the exhaust 42 from the flow through the tubing 32, in second subtraction element 82.

Calculation of Moving Average Ventilation

Figure 3:
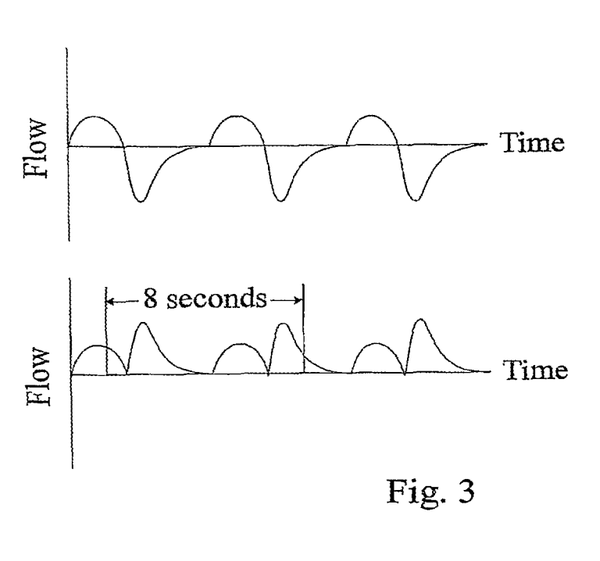
FIG. 3 shows the portion of the absolute value of a flow function used to calculate ventilation.

As depicted in FIG. 3, the instantaneous or short term ventilation is calculated as half the $\vartheta_{ma}$ second moving average of the absolute value of a $<_{RA}$ Hz low pass filtered respiratory airflow. The instantaneous ventilation is required for detection of hypopneas. Since hypopneas can be as short as 10 seconds, the window over which instantaneous ventilation is calculated should be less than 10 seconds. Conversely, a single breath is typically 5 seconds. Hence instantaneous ventilation should be calculated over periods of at least 5 seconds. Therefore a preferred value for $\vartheta_{ma}$ is 8 seconds. By using a moving window, instantaneous ventilation is always defined, regardless of the point in the respiratory cycle. Taking half the absolute value of the flow signal is identical to taking the average of the inspiratory and expiratory flows. A preferred value for $<_{RA}$ is 1 Hz is to prevent non-respiratory noise (snore, cardiogenic airflow) being included in the measurement of ventilation.

The preferred long term moving average ventilation is calculated as follows:

initialize at each mask-off to mask-on transition to 7.5 L/min for the next 2 minutes, low pass filter the flow with time constant of 20 seconds thereafter, low pass filter the flow with a time constant of 100 seconds, however, cease to update the long term ventilation while an apnea/hypopnea (as determined below) is in progress.

The 100 second time constant is chosen to be long compared with the duration of a typical apnea or hypopnea (20-seconds), but short compared with genuine changes in ventilation, for example with the sleep state (many minutes). The initialization to 7.5 L/min (a typical normal value), rather than zero, is so that, in the case of normal breathing, the long-term average will reach the true value more quickly. The reduced time constant for the first 2 minutes also aids in faster settling to the correct value.

Detection of Apnea

Figure 4:
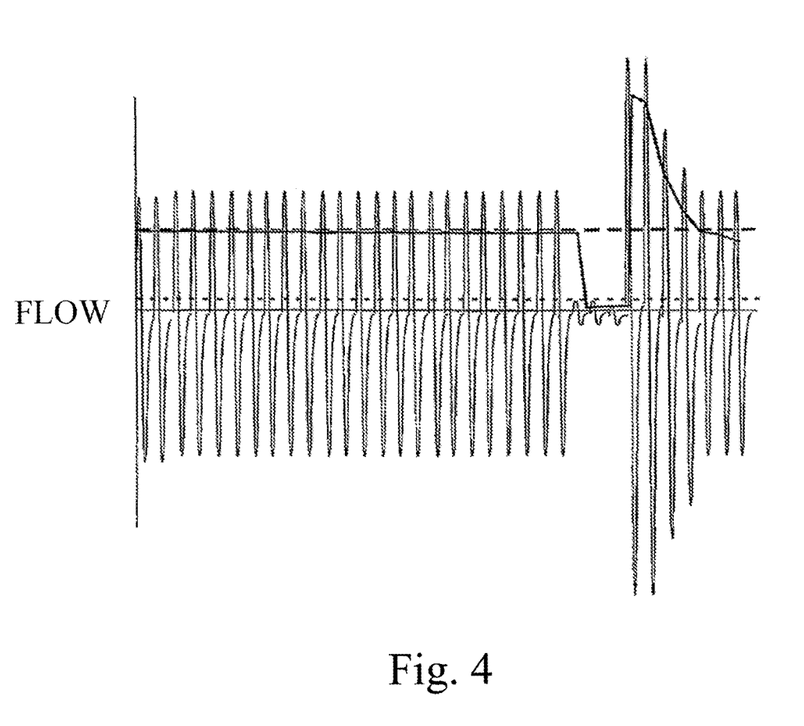
FIG. 4 shows a typical apnea following a period of normal breathing and the result of calculating long term averages and thresholds.
Figure 5:
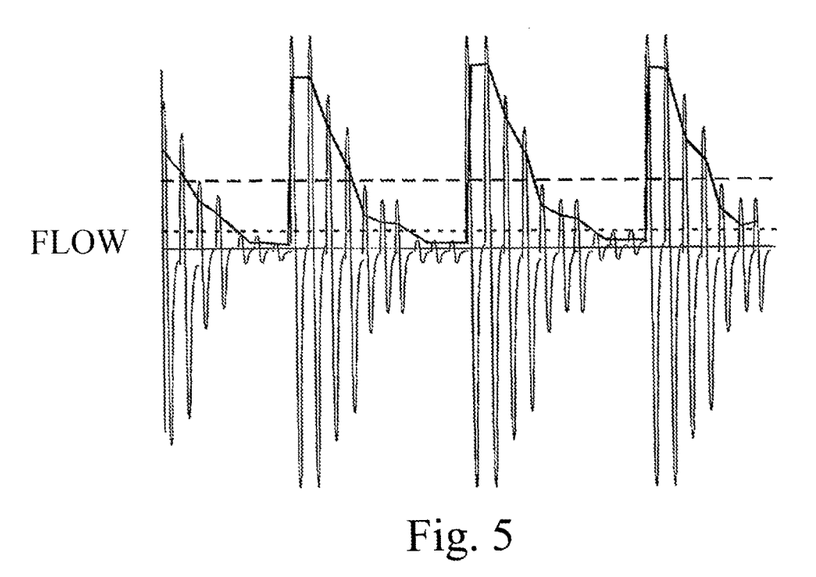
FIG. 5 shows a breathing pattern involving several apneas in succession.

FIG. 4 shows a typical single 15 second apnea following a period of normal breathing of 24 breaths. In that figure, the dashed line shows the long-term averaged ventilation. The dotted line is a threshold set at 25% of the longterm average flow. The solid line is a two second moving average flow and becomes very small during the apnea, below the threshold.

Where there are several apneas, as shown in FIG. 5, the longterm average ventilation would be affected. Accordingly, in the present invention, the averaging of the long term ventilation is suspended upon detection of a short term ventilation falling below the threshold, which indicates an apnea.

Hypopnoea Detection

Figure 6:
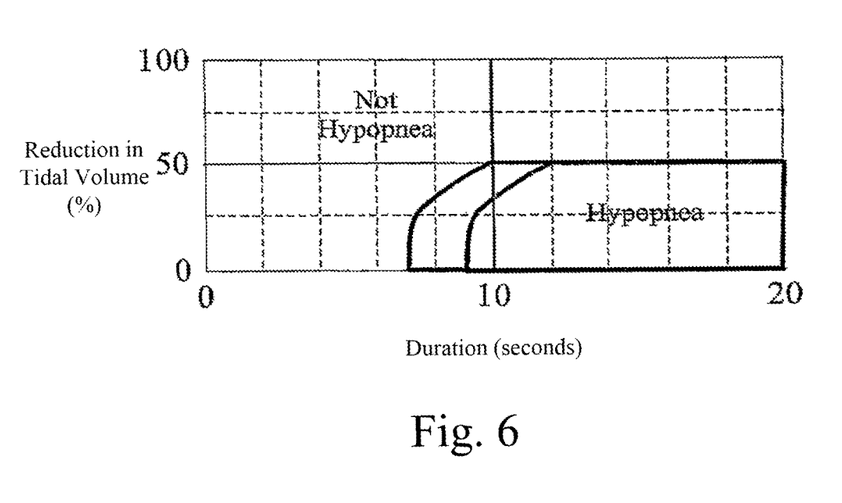
FIG. 6 shows a graph of the reduction of tidal volume versus event duration.

A hypopnoea is scored if the short term ventilation drops below 0.5 times the longterm average minute ventilation (in L/sec) and hypopneas are scored if the ventilation is reduced by 50% for at least 10 seconds. Mathematically, this definition implies convolving the respiratory waveform with a 10 second rectangular window, which will make it impossible in principle to precisely measure the length of a hypopnea to the nearest second. Therefore, as shown in FIG. 6, on a graph of reduction of tidal volume versus event duration, there is a region to be scored as a hypopnea, a region to be not scored as a hypopnea, and a "don't care" region, whose shape is based on spreadsheet simulations.

Termination of Apnea/Hypopnea

To determine the termination of the apnea/hypopnea a score is maintained as to how many data points of short term ventilation are above or below the threshold. Then, periodically, the score is checked. If the number of data points below the threshold is greater than those above it is assumed the apnea is continuing, otherwise the apnea/hypopnea event is considered to have ended.

Steps for Apnea/Hypopnea Detection

Figure 7:
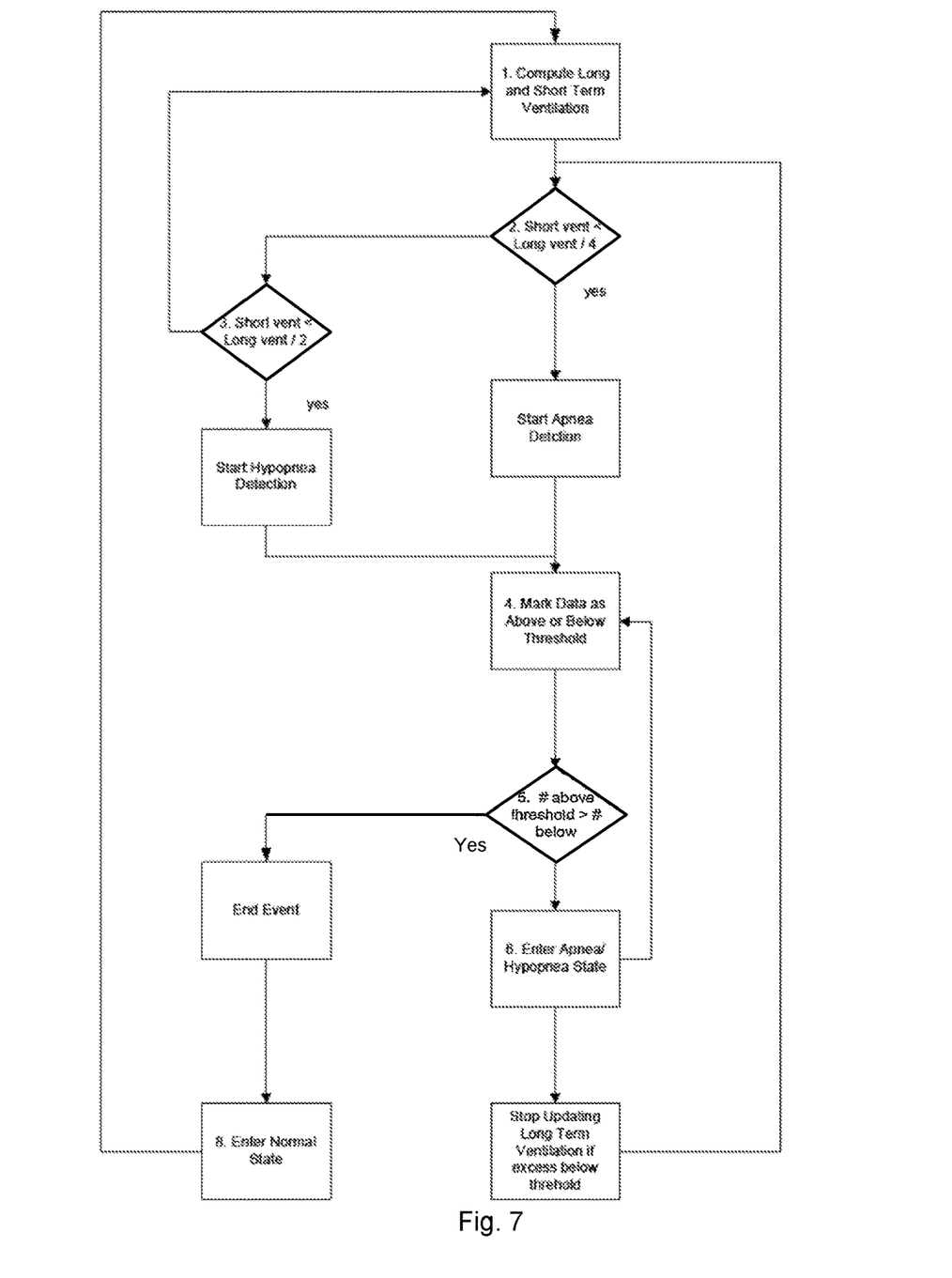
FIG. 7 shows a flow chart of an algorithm of the present invention.

A logical diagram of the novel algorithm of the present invention is depicted in FIG. 7. The steps are as follows:

1. Take the absolute value of flow and compute short-term ventilation and long term ventilation using IIR filters. Do not update long term ventilation filter if apnea is detected or, hypopnea is detected for more than 10 sec.
2. If short-term vent<long-term vent/4 start apnea detection, initialize duration=2 sec.
3. If short-term vent<long-term vent/2 start hypopnea detection, initialize duration=2 sec
4. for the next 8 sec, keep marking apnea/hypopnea data as above or below the respective thresholds.
5. at the end of 8 sec if number of data below threshold is greater than number of data above threshold, enter apnea and/or hypopnea state
6. from now on every 4 sec period, keep marking data as above or below threshold (and incrementing apnea duration).
7. At the end of each period, check if number of data below threshold is greater than number of data above threshold+10.
8. If false record apnea/hypopnea and enter normal state, otherwise continue.

More complex variants of CPAP therapy, such as bi-level CPAP therapy or therapy in which the mask pressure is modulated within a breath, can also be monitored and/or controlled using the methods described herein.

The invention claimed is:

1. An apparatus for detecting occurrence of either or both of apnea and hypopnea events in a patient comprising:
   a sensor for sensing respiratory flow;
   a first filter to iteratively calculate a first average respiratory airflow over a first time interval;
   a second filter to iteratively calculate a second average respiratory airflow over a second time interval, the second time interval being shorter than the first time interval; and
   a controller in communication with said sensor and the first and second filters, the controller programmed to iteratively:
      calculate a predetermined fraction of the first average respiratory airflow;

compare the second average respiratory airflow to the predetermined fraction of the first average respiratory airflow;
determine a commencement of an apnea or hypopnea event based on the comparison;
continue to calculate the second average respiratory airflow to confirm an occurrence of the apnea or hypopnea event;
wherein confirming an occurrence comprises:
maintaining a first value representing a number of times the second average respiratory airflow is less than the predetermined fraction of the first average respiratory airflow;
maintaining a second value representing a number of times the second average respiratory airflow is not less than the predetermined fraction of the first average respiratory airflow; and
comparing the first value to the second value; a controllable positive airway pressure device operable to produce breathable gas at a treatment pressure, wherein the controller is further programmed to adjust the treatment pressure based on determining the occurrence of the apnea or hypopnea event.

2. The apparatus of claim 1, wherein the predetermined fraction is approximately ¼.

3. The apparatus of claim 1, wherein the predetermined fraction is approximately ½.

4. The apparatus of claim 1, wherein the controller is programmed to determine the commencement of the apnea or hypopnea event when the second average respiratory airflow is less than the predetermined fraction of the first average respiratory airflow.

5. The apparatus of claim 1, wherein the controller is further programmed to detect an end of the apnea or hypopnea event by determining when the second average respiratory airflow remains above the predetermined fraction of the first average respiratory airflow.

6. The apparatus of claim 1, wherein the first time interval is a one hundred seconds time constant.

7. The apparatus of claim 6, wherein the first time interval is initially set to a shorter time constant to allow a correct average respiratory airflow value to be determined faster.

8. The apparatus of claim 1, wherein the first average respiratory airflow is initially preset to a predetermined value.

9. The apparatus of claim 8, wherein the predetermined value is approximately 7.5 liters per minute.

10. The apparatus of claim 1, wherein the second time interval is a period of less than ten seconds.

11. The apparatus of claim 10, wherein the second time interval is a period of at least five seconds.

12. The apparatus of claim 11, wherein the second time interval is eight seconds.

13. The apparatus of claim 1, wherein the controller is programmed to record a number of apnea and/or hypopnea events that have occurred.

14. The apparatus of claim 1, wherein at least one of the first and second filters is an infinite impulse response (IIR) filter.

15. The apparatus of claim 1, wherein upon confirming the occurrence of an apnea or hypopnea event, the controller is further programmed to determine patency of an airway using a forced oscillation method and to classify the airway based on the determined patency as a closed airway, a partially obstructed airway or an open airway.

16. The apparatus of claim 1, wherein the controller is further programmed to, upon determining the commencement of an apnea or a hypopnea event, suspend calculation of the first average respiratory airflow until the apnea ends or the hypopnea ends.

17. A method for detecting an occurrence of an apnea or a hypopnea event with a continuous positive airway pressure (CPAP) device including a programmed controller, comprising:
obtaining data indicative of a person's respiratory airflow;
iteratively calculating a first average respiratory airflow over a first time interval;
iteratively calculating a second average respiratory airflow over a second time interval, the second time interval being shorter than the first time interval;
calculating a predetermined fraction of the first average respiratory airflow;
comparing the second average respiratory airflow to the predetermined fraction of the first average respiratory airflow;
determining a commencement of an apnea or hypopnea event based on the comparison;
continuing to calculate the second average respiratory airflow to confirm occurrence of the apnea or hypopnea event;
wherein confirming an occurrence comprises:
determining a first value representing a number of times that the second average respiratory airflow is less than the predetermined fraction of the first average respiratory airflow over a period of time;
determining a second value representing a number of times that the second average respiratory airflow is not less than the predetermined fraction of the first average respiratory airflow over the period of time; and
comparing the first value to the second value; supplying a breathable gas to the person's airway at a treatment pressure; and adjusting the treatment pressure based on determining the occurrence of the apnea or hypopnea event.

18. The method of claim 17, wherein the predetermined fraction is approximately one quarter.

19. The method of claim 17, wherein the predetermined fraction is approximately one half.

20. The method of claim 17, wherein the commencement of the apnea or hypopnea event is determined when the second average respiratory airflow is less than the predetermined fraction of the first average respiratory airflow.

21. The method of claim 17, further comprising detecting an end of the apnea or hypopnea event by determining when the second average respiratory airflow remains above the predetermined fraction of the first average respiratory airflow.

22. The method of claim 17, wherein the first time interval is a one hundred seconds time constant.

23. The method of claim 22, wherein the first time interval is initially set to a shorter time constant to allow a correct average respiratory airflow value to be determined faster.

24. The method of claim 17, wherein the first average respiratory airflow is initially preset to a predetermined value.

25. The method of claim 24, wherein the predetermined value is approximately 7.5 liters per minute.

26. The method of claim 17, wherein the second time interval is a period of less than 10 seconds.

27. The method of claim 26, wherein the second time interval is a period of at least 5 seconds.

28. The method of claim 27, wherein the second time interval is 8 seconds.

29. The method of claim 17, further including:
scoring by the controller the occurrence of an apnea or hypopnea, and
recording by the controller a number of apnea and/or hypopnea events that have occurred.

30. The method of claim 17, further including:
wherein either the first average respiratory airflow or the second average respiratory airflow or both are calculated using an infinite impulse response (IIR) filter.

31. The method of claim 17, wherein upon confirming the occurrence of an apnea or hypopnea event, further including:
determining, by the controller, patency of an airway using a forced oscillation method, and
classifying, by the controller, the airway based on the determined patency as a closed airway, a partially obstructed airway or an open airway.

32. The method of claim 17, further comprising suspending, upon determining the commencement of an apnea or a hypopnea event, the calculation of the first average respiratory airflow until the apnea ends or the hypopnea ends.

\* \* \* \* \*